United States Patent [19]

Threlkel

[11] Patent Number: 4,959,491

[45] Date of Patent: Sep. 25, 1990

[54] DETERGENT GRADE OLEFINS, ALKYLBENZENES AND ALKYLBENZENE SULFONATES AND PROCESSES FOR PREPARING

[75] Inventor: Richard S. Threlkel, El Cerrito, Calif.

[73] Assignee: Chevron Research Company, San Francisco, Calif.

[21] Appl. No.: 24,742

[22] Filed: Mar. 11, 1987

[51] Int. Cl.$^5$ ................. C07C 2/26; C07C 143/24
[52] U.S. Cl. ................. 562/94; 585/455; 585/511
[58] Field of Search ........... 585/511, 502, 455, 511; 502/117; 260/505 A; 562/94

[56] References Cited

U.S. PATENT DOCUMENTS 3,315,009  4/1967  Engelbrecht .
3,317,628  5/1967  Schuck .
3,424,815  1/1969  Cannell et al. .................. 502/117
4,069,273  1/1978  Komoto .......................... 585/511

FOREIGN PATENT DOCUMENTS 534167  12/1956  Canada ......................... 260/505 A
645195  10/1950  United Kingdom ........... 260/505 A
825952  12/1959  United Kingdom ........... 260/505 A

*Primary Examiner*—Alan Siegel
*Attorney, Agent, or Firm*—C. J. Caroli; L. S. Squires; R. C. Gaffney

[57] ABSTRACT

A two-step dimerization process for producing semi-linear $C_{12}$ olefins using homogeneous dimerization catalysts and new $C_{12}$ olefins mixtures. The $C_{12}$ product is especially useful for the production of biodegradable sulfonated alkylaryl detergents and intermediates therefor.

31 Claims, No Drawings

DETERGENT GRADE OLEFINS, ALKYLBENZENES AND ALKYLBENZENE SULFONATES AND PROCESSES FOR PREPARING

BACKGROUND OF THE INVENTION

This invention relates to the polymerization of olefins to produce longer chained olefin products. In a further aspect, the invention relates to the production of olefins and alkylbenzenes which are especially useful as intermediates in the production of alkylbenzene sulfonate detergents. The invention also relates to such detergents and their production.

One significant commercial application of longer chained olefins (e.g., $C_{10}$ to $C_{15}$) is as intermediates in the production of alkyl aromatic sulfonate detergents. Since large amounts of such detergents are ultimately released to the environment, the need for biodegradability is well recognized. It is further well recognized that linear and mono-branched alkyl aromatic sulfonates are generally much more readily biodegraded than multi-branched alkyl aromatic sulfonates and, hence, much more desirable as detergents. Thus, the need for processes which efficiently produce high yields of $C_{10}-C_{15}$ linear or semi-linear olefins or olefin mixtures which afford biodegradable alkylbenzene sulfonates.

U.S. Pat. No. 3,315,009 discloses a two-dimerization step process for preparing $C_8-C_{16}$ olefins using a heterogeneous cobalt oxide catalyst. Patentee teaches that it is preferred that the dimer feed to the second stage dimerization be substantially linear, but that the presence of branched-chain mono-olefins in the feed to the second stage up to 15% by weight is not deleterious.

U.S. Pat. No. 3,317,628 discloses a two-dimerization step process for preparing higher olefins similar to that described in the aforementioned patent, but using a somewhat different heterogeneous cobalt catalyst. Patentee stresses one of the advantages of patentee's process is that the formation of undesired isomers, such as 2-methylpent-2-ene is minimized if not eliminated. Patentee describes 2-methylpent-2-ene as an especially undesirable isomer in hexene fractions for the purpose of patentee's process because it is not separated from n-hexene by commercial methods of distillation and therefore requires special separation procedures or it must remain as an impurity.

U.S. Pat. No. 3,402,217 discloses a two zone polymerization process for preparing higher olefins using a molecular sieve or zeolite catalyst. Patentee teaches that a particularly preferred mono-olefin dimer feed to the second zone polymerization is one which contains no greater than 10% by weight of branched-chain mono-olefins and the remainder straight-chain mono-olefins. Patentee further teaches that generally ordinary fractional distillation is adequate to purify the first dimerization zone product, but that in addition to or in place of fractional distillation, other conventional separation or purification means such as adsorbents, i.e., molecular sieves, solvent extraction, extractive distillation, selective polymerization, isomerization, and the like may be employed to conform the dimer product of the first-stage dimerization to the feed requirements of the second-stage dimerization. Patentee states that it is immaterial to patentee's invention what separation means is used for purifying the product of the first-stage dimerization to meet the feed requirements of the second-stage dimerization, so long as such separation means provides the desired purification.

U.S. Pat. No. 3,409,703 discloses a two-dimerization step process similar to that disclosed in U.S. Pat. No. 3,315,009, but using a modifying agent in the first dimerization.

The recovery of isobutylene from C-4 hydrocarbon streams is reportedly disclosed in Belgium Patent No. 851,832; Japanese Patent Application No. 49061102; *Chem. Abstracts*, Vol. 83-179515; and *Khim Prom*, Vol. 41, No. 8, 625–26 (August 1965).

U.S. Pat. No. 3,424,815 describes the preparation of alpha-olefin oligomers using a catalyst comprising the product of certain nickel chelates with a halide-free organoaluminum compound such as alkyl aluminum alkoxides. Patentee teaches that the nickel chelating ligand-anion is substituted with electron withdrawing groups, i.e., nitro, halo, cyano or carboalkoxy and that superior results are obtained when the chelating ligands are halogenated organic ligands.

U.S. Pat. No. 3,592,870 discloses olefin dimerization process using a catalyst formed from an organoaluminum compound and one of the following nickel complexes: (a) bis(beta-mercaptoethylamine)nickel (II) complex; (b) alpha-diketobis(beta-mercaptoethylimine)-nickel (II) complex; (c) S,S,-disubstituted bis(beta-mercaptoethylamine)nickel (II) complex; or (d) S,S,-disubstituted-alpha-diketone bis(beta-mercaptoethylimine)-nickel (II) complex. Based on the product distribution shown in the examples of this patent, the polymerization of propylene using patentee's catalysts $C_6$ olefin products containing 63 to 70% branched olefins depending on the particular catalyst used.

U.S. Pat. No. 4,069,273 describes a process for dimerizing low molecular weight linear alpha-olefins using a complex of bis(1,5-cyclooctadiene)nickel and hexafluoro-2,4-pentanedione as a homogeneous catalyst. Patentee describes his process as producing a highly linear olefin product. U.S. Pat. No. 4,366,087 describes a process for oligomerizing olefins using a catalyst containing a nickel compound having the formula $(R_1COO)(R_2COO)Ni$, wherein $R_1$ is a hydrocarbyl radical having at least 5 carbon atoms and $R_2$ is a haloalkyl radical and an organic aluminum halide. As can be seen from the examples in this patent, patentee's process afforded a product containing a large amount of branched olefins. A number of catalyst systems used for the polymerization of olefins are described in *Chemical Review*, 86 (1986), pp. 353–399.

Although the prior art speaks in glowing terms of highly linear products, seldom are such results obtained except at the cost of low yields or other disadvantages. For example, the two-step processes of the prior art which produce highly linear $C_{10}-C_{15}$ olefin products also generally require a highly linear intermediate product, thus effectively wasting significant yields of methyl pentenes which are obtained in the first step reaction product. The prior art systems using heterogeneous catalysts suffer from the usual contact problems incident to such catalysts. Moreover, the heterogeneous catalysts used by the prior art are frequently difficult and expensive to prepare. The use of halide modifying agents also presents a problem since such agents are generally very corrosive and presents equipment problems.

Thus, there is a need for better processes for producing detergent grade $C_{10}-C_{16}$ olefins.

SUMMARY OF THE INVENTION

The present invention provides a two-dimerization step process which efficiently produces good yields of detergent grade olefins and in one embodiment increases catalyst life. The present invention also provides a novel mixture of biodegradable $C_{12}$ olefins.

In one embodiment, the present invention provides a process comprising the steps of:

(a) contacting propylene with a dimerization catalyst under dimerization conditions to produce a higher olefin product containing at least 60% by weight of linear hexenes and the remainder higher olefins and branched $C_6$ olefins;

(b) fractionally distilling the product of step (a) to remove $C_9$ and higher olefins and recovering a $C_6$ olefin fraction containing about from 70 to 82% by weight linear hexenes;

(c) contacting the $C_6$ olefin fraction of step (b) with a homogeneous dimerization catalyst under dimerization conditions to produce a highly semi-linear $C_{12}$ olefin product containing at least 60% by weight of linear $C_{12}$ olefins and mono-branched $C_{12}$ olefins.

In a further embodiment of the above-described process the $C_6$ olefin fraction is treated with sulfuric acid and phase separated to produce an enriched linear hexane product containing about from 80 to 90% by weight n-hexenes which is used as the reactant for the second polymerization.

In a further embodiment, the invention provides a novel mixture of $C_{12}$ olefins which can be used to prepare alkylbenzene sulfonate detergents. It has been discovered that by conducting the $C_6$ olefin fractionation [step (b)] to provide a $C_6$ olefin fraction containing about 70 to 75% by weight linear hexene that the $C_{12}$ olefin reaction product contains a relatively large amount (e.g., about 10 to 40% by weight or typically 15 to 35% by weight) of multibranched olefins. This would normally be considered a substantial disadvantage, particularly under U.S. environmental standards, because multibranched olefins are considered unsuitable for detergent use (i.e., as intermediates for alkylbenzene sulfonates) because of poor biodegradability. Surprisingly it has been discovered that the particular $C_{12}$ olefin mixture provided by this embodiment produces alkylbenzene sulfonates having adequate biodegradability for commercial detergent use. This affords a substantial economic advantage because of the lower costs involved in making such olefins.

The invention also provides a method for preparing $C_{12}$ alkylbenzenes and alkylbenzene sulfonates which comprises the additional step of contacting the $C_{12}$ olefin product of the aforementioned processes with benzene in the presence of an alkylating catalyst under reactive conditions thereby yielding said $C_{12}$ alkylbenzene and optionally contacting said $C_{12}$ alkylbenzene with a sulfonating agent under reaction conditions to yield the corresponding $C_{12}$ alkylbenzene sulfonic acid and neutralizing said $C_{12}$ alkylbenzene sulfonic acids with a base to yield the corresponding detergent $C_{12}$ alkylbenzene sulfonate salt.

Where the aforedescribed mixture of $C_{12}$ olefins of the present invention are used in the benzene alkylation reaction, the corresponding $C_{12}$ alkylbenzenes, and $C_{12}$ alkylbenzene sulfonic acids and detergent salts thereof are also novel and are encompassed by the present invention.

Additional aspects of the invention will also be apparent from the further description of the invention which follows below.

FURTHER DESCRIPTION OF THE INVENTION AND PREFERRED EMBODIMENTS

The first step of the present process comprises contacting propylene with a homogeneous dimerization catalyst under reactive conditions. The propylene feed should contain at least about 90% propylene and although it may contain other alkenes it should be essentially free of dienes. Preferably the propylene feed should also be substantially free of ethylene.

Typically, the dimerization is conducted at temperatures in the range of about from 30° to 100° C., preferably 50° to 80° C. for about from ½ to 8 hours, preferably 1 to 5 hours, using a propylene to catalyst mole ratio of about 200 to 20,000, preferably 1,000 to 10,000 moles of propylene per mole of catalyst. The dimerization is generally conducted as a liquid phase reaction using pressures in the range of about 1 to 50 atmospheres, preferably 10 to 40 atmospheres.

It is important that the first step polymerization provide an initial reaction product mixture containing at least about 60% by weight linear hexenes. The remainder of the product comprises higher olefins (i.e., $C_9$ olefins and above) and branched $C_6$ olefins. After removal of both the propylene and higher olefins the remaining $C_6$ olefin mixture should contain about from 70 to 82% b weight of linear hexenes and in terms of producing a highly linear product preferably about 75 to 82% by weight linear hexene. Higher amounts of linear hexene do not adversely affect the present process, but generally are not obtained from the first stage without specialized extraction steps. By using a $C_6$ olefin mixture containing only about 70 to 75% by weight linear hexene in the second step polymerization, the $C_{12}$ olefin product mixture of the present invention is obtained having poorer linearity. However, despite this poor linearity, the $C_{12}$ product mixture has been found to produce alkylbenzene sulfonates having adequate biodegradability to be commercially used as detergents.

The selection of the catalyst for the first step dimerization is particularly important. Thus, I have found that the required yields and selectivity can be obtained by using certain nickel complex catalysts as the first-step dimerization catalyst, under the conditions indicated above, whereas cobalt derivative catalysts have generally produced inadequate results. Suitable nickel complex catalysts which can be used are, for example, described in U.S. Pat. Nos. 3,424,815; and 4,069,273; and in my copending application Ser. No. 896,897, filed on Aug. 15, 1986, the entire disclosures of all of which, are hereby incorporated by reference. Such catalysts include catalysts selected from the following groups:

(1) catalysts comprising the product of a nickel chelate having the formula

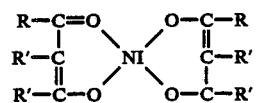

wherein R and R' independently are hydrogen, alkyl or aryl of up to 10 carbon atoms, or haloalkyl or haloaryl of up to 10 carbon atoms, with the proviso that the two R' groups of each chelating ligand together with the adjacent carbon atoms to which they are attached, can form a six-membered carbocyclic aromatic ring of up to 4 halogen substituents. The halogenated chelating ligand preferably has up to 15 carbon atoms and from 2 to 8 halogen substituents, but more preferably has up to 10 carbon atoms and from 3 to 6 halogen substituents. The halogen substituents of the chelating ligand are suitably fluorine, chlorine, bromine or iodine, but best results are obtained when the halogen substituents are halogen of atomic number from 9 to 17 inclusive, that is, are fluorine or chlorine or wherein the R' groups together form a divalent radical in which the monoenol configuration is maintained as part of the aromatic ring; with an alkyl aluminum alkoxide having the formula $(R'')_m Al(OR'')_n$ wherein each R'' independently is alkyl of up to carbon atoms, preferably of up to 4 carbon atoms, m is a whole number from 1 to 2 inclusive and n is a whole number from 1 to 2 inclusive selected so that the sum of m and n, i.e., the term (m+n), equals 3;

(2) a catalyst composition complex prepared by the reaction of bis(1,5-cyclooctadiene)nickel(O) and hexafluoro-2,4-pentanedione; or (3) catalyst compositions comprising (1) a transition metal complex selected from complexes of nickel and palladium with a fluoro-organic thiol or sulfide ligand, having a single sulfur atom in a ligating position and wherein the carbon atom adjacent the carbon atom to which the sulfur atom is attached has at least one fluoro substituent and with the proviso that said fluoro-organic thiol or sulfide does not contain any other ligating group or atom in a ligating position which will displace fluoro as a ligand, and (2) an organometallic-reducing agent selected from the group of borohydride and organoaluminum halides and alkoxides having the formula $R^*_m AlX_n$ wherein $R^*$ is alkyl, aryl or arylalkyl; X is fluoro chloride, bromide, iodide or alkoxide and m is 1 or 2 and n is 3-m. Preferably the fluoro-organic thiol or sulfide is selected from the group having the formula $R_1SR$ wherein $R_1$ is fluoroalkyl having 1 to 18 fluoro atoms and 1 to 8 carbon atoms; fluoroaryl having 6 to 10 carbon atoms and 1 to 6 fluoro atoms; fluoroalkenyl having 2 to 8 carbon atoms and 1 to 16 fluoro atoms; fluoroalkanoyl having 2 to 8 carbon atoms and 1 to 15 fluoro atoms, fluoroalkanoylalkylene having 1 to 17 fluoro atoms and having 2 to 8 carbon atoms in the alkanoyl moiety and 1 to 6 carbon atoms in the alkylene moiety or fluorobenzoyl having 1 to 5 fluoro atoms or a substituted group selected from the fluoro-substituted groups set forth above, further substituted with 1 to 6 substituents independently selected from the group of lower alkyl, lower haloalkyl having 1 to 4 halo substituents, halo, lower haloalkenyl having 1 to 4 halo substituents, or lower alkoxy; and R is hydrogen, $C_1$-$C_8$ alkyl; $C_2$-$C_8$ alkenyl, aryl having 6 to 10 carbon atoms or arylalkyl, having 6 to 10 carbon atoms in aryl moiety and 1 to 4 carbon atoms in the alkyl moiety; alkanoyl having 2 to 8 carbon atoms; alkanoylalkylene having 2 to 8 carbon atoms in the alkanoyl moiety and 1 to 4 carbon atoms in the alkylene moiety; or a substituted group selected from the same groups as set forth hereinabove with respect to R substituted with from 1 to 6 substituents independently selected from the group of lower alkyl, lower haloalkyl having 1 to 4 halo substituents, halo, lower haloalkenyl having 1 to 4 halo substituents or lower alkoxy.

Examples of specific catalysts which can be used include: hexafluoroacetoacetyl nickel cyclooctadiene; bis[pentafluorophenylthio]nickel with triethyl aluminum sesquichloride, [i.e., $(C_2H_5)_3Al_2Cl_3$]; hexafluoroacetoacetyl nickel hexanoate with diethylaluminum ethoxide, and the like. Generally, excellent results are obtained by using hexafluoroacetoacetyl nickel cyclooctadiene as the first step catalyst.

In the next step of the process, $C_9$ and higher olefins are removed by fractional distillation. This can be effected by conventional distillation procedures which are well known to the art. Unreacted propylene is removed in this step or simply flashed off prior to the distillation and preferably recycled back to the propylene feed stream. Hexenes are recovered in a distillation fraction comprising linear hexene and branched C-6 olefins.

In a further embodiment, it has been discovered that by treating the aforementioned linear hexene and branched $C_6$ olefin distillation fraction with sulfuric acid that as well as producing a more linear olefin product from the second step dimerization that the effective life of the second-step dimerization catalyst is greatly increased.

The acid treatment can be effected by acidifying the hexene fraction with aqueous 50 to 90 weight % sulfuric acid, preferably 70 to 85 weight % sulfuric acid at 0° to 40° C., preferably 5° to 25° C. Acid treatment results in the protonation of only branched olefins which have a branching substituent at a double bond carbon atom such as, for example, 2-methyl-2-pentene [$CH_3CH_2CH=C(CH_3)CH_3$] and 2-methyl-1-pentene [$CH_3CH_2CH_2C(CH_3)=CH_2$] producing sulfate products which are soluble in the aqueous sulfuric acid. The straight chain olefins and other branched chained olefins are unreactive below 30° C. and remain insoluble and form an immiscible layer with the aqueous sulfuric acid. Thus, by this means, the major isomers contributing to the percent branching of the hexenes can be selectively phase separated in the aqueous sulfuric acid phase from the immiscible hydrocarbon phase. Depending on the acid concentration, the percent linear olefin content of the enriched hexenes phase will be at least about 80% by weight and generally will vary from about 80 to 90% by weight. Depending on the concentration of olefin sulfates and the strength of the acid in the recovered acid phase, the spent or partially spent acid phase may be reused directly or regenerated. The spent or partially spent acid can be regenerated by simple warming to 50° to 120° C., preferably 60° to 80° C. for 10 to 150 minutes, preferably 20 to 40 minutes. This causes the protonated branched methyl-pentenes to dimerize affording a mixture of branched dodecenes and sulfuric acid. The branched dodecenes are immiscible with the sulfuric acid phase. Thus the acid phase can then be separated, and if desired reused in the acid treatment, by simple phase separation.

In the second dimerization step of the present process, the enriched hexene product, either with or without the aforementioned sulfuric acid treatment, is contacted with a suitable dimerization catalyst under dimerization conditions. This dimerization is typically conducted at temperatures in the range of about from 0° to 100° C., preferably 10° to 80° C. for about from ½ to 8 hours, preferably 1 to 4 hours, using $C_6$ olefin catalyst mole ratios in the range of about 200:1 to 10,000:1, preferably 500:1 to 5,000:1 moles of $C_6$ olefins per mole of catalyst. Typically, the polymerization is conducted as a liquid phase reaction and is conducted at pressures in the range of about 1 to 10 atmospheres, preferably 1 to 5 atmospheres. The dimerization affords a product typically containing at least 60% by weight of semi-linear $C_{12}$ olefins (i.e., dodecane and mono-branched $C_{12}$ olefins) which is highly useful as an intermediate in the manufacture of alkyl aromatic detergents. As before mentioned, in the case where the feed to the second step polymerization is only 70 to 75% linear hexene, the resulting $C_{12}$ olefin product contains a relatively high amount (e.g., 10 to 40% by weight, typically 15 to 35% by weight) of multibranched $C_{12}$ olefins, which normally would be considered unsuitable to prepare detergent alkylbenzene sulfonates because of poor biodegradability, but surprisingly have been found to produce novel $C_{12}$ alkylbenzene mixtures and $C_{12}$ alkylbenzene sulfonates which have good biodegradability despite the relatively large amount of branched $C_{12}$ alkylbenzene sulfonates contained therein. It should also be appreciated that where the feed to the second polymerization contains more than 75% linear hexene, a highly semi-linear $C_{12}$ olefin product is obtained.

A homogeneous catalyst is also used in the second step dimerization. However, the requirements for the catalyst for the second step dimerization are not as stringent as for the first step dimerization and a wide range of olefin dimerization catalysts can be used for the second step. Thus, the catalysts described above with respect to the first step dimerization can be used for the second step dimerization as well as catalyst such as nickel bis[carboxylates] with $C_1$-$C_6$ alkyl aluminum halides; carbonyl nickel phosphines, phosphites, thiolates [for example, those having the formula $(C=O)_{4-n}NiL_n$ wherein L is phosphines, phosphites, thiolates, e.g., aryl phosphine, alkyl phosphines, etc.]; and n is 1, 2, or 3, with Lewis acids (for example, aluminum chloride, boron fluoride, etc.).

Generally, excellent results are obtained using hexafluoroacetoacetyl nickel cyclooctadiene; bis[pentafluorophenylthio]nickel with triethyl aluminum sesquichloride; bis[triphenylphosphino]nickel dicarbonyl with aluminum chloride or nickel 2-ethylhexanoate trifluoroacetate with diethyl bis-aluminum tetrachloride or ethyl aluminum dichloride as the second-step catalyst.

The catalyst and unreacted $C_6$ olefins are typically separated from the reaction production by fractional distillation or any other suitable procedure. Higher olefins can also be separated by fractional distillation.

$C_{12}$ alkylbenzenes can be prepared by contacting the aforedescribed $C_{12}$ olefin product with benzene in the presence of a suitable alkylation catalyst (e.g., hydrogen fluoride, aluminum chloride, and the like) under reactive conditions.

Typically, where hydrogen fluoride is used as the catalyst, the alkylation is conducted at temperatures in the range of about from −20° to 65° C., preferably 0° to 55° C., for about ½ to 4 hours, preferably 1 to 2 hours, using mole ratios in the range of about from 5 to 50, preferably 10 to 20 moles of benzene per mole of olefin and catalyst mole ratios in the range of about from 0.25 to 4, preferably 1 to 1.5 moles of benzene per mole of catalyst (i.e., hydrogen fluoride). Because the presence of water in reactions using hydrogen fluoride is known to present corrosion problem, the alkylation is preferably conducted under anhydrous conditions. The $C_{12}$ alkylbenzene(s) can be recovered from the reaction product by any suitable procedure, for example, by phase separating the $C_{12}$ alkylbenzene rich product phase from the hydrogen fluoride phase; neutralizing any remaining hydrogen fluoride in the $C_{12}$ alkylbenzene phase; and removing unreacted benzene by distillation.

In the case where aluminum chloride is used as the catalyst, the reaction is conditioned in the presence of acid at temperatures in the range of about 0° to 75° C., preferably 25° to 50° C. for about from ½ to 4 hours, preferably 1 to 2 hours using about from 5 to 50, preferably 10 to 20 moles of benzene per mole of olefin and about from 2 to 8, preferably 3 to 5 moles of benzene per mole of aluminum chloride catalyst. Typically, the presence of the acid is ensured by simply saturating the benzene reactant with an acid such as hydrogen chloride. The $C_{12}$ alkylbenzene can be recovered from the reaction product by any suitable procedure such as, for example, aqueous extraction to remove aluminum chloride followed by neutralization and distillation. The $C_{12}$ alkylbenzene product can be separated from the reaction product mixture by any suitable procedure. Typically, the catalyst is simply decanted off and any remaining catalyst reaction mixture neutralized. The reaction product can then be purified by distillation to remove unreacted benzene, etc.

Regardless of the catalyst used, the alkylation is typically conducted as a liquid phase reaction and is typically conducted at pressures in the range of about from 1 to 10 atmospheres, preferably 1 to 5 atmospheres.

The sulfonation can be conducted by contacting the $C_{12}$ alkylbenzene product of the aforedescribed process with a sulfonating agent, either neat, or optionally in an inert organic solvent or liquid medium, under reaction conditions. The sulfonation can also be conducted in the presence of a moderating agent, such as, for example, dioxane. The modifying agent (e.g., dioxane) complexes with the sulfonating agent (e.g., sulfur dioxane) thus moderating the speed or intensity of the reaction.

The sulfonation is typically conducted at temperatures in the range of about from −40° to 100° C., preferably 0° to 50° C. for about from 1 to 20 hours, preferably 1 to 10 hours using pressures of about from ½ to 5 atmospheres, preferably 1 to 2 atmospheres. Typically, about from 1 to 1.5, preferably about from 1.05 to 1.25 moles, based on sulfur, of sulfonating agent are used per mole of $C_{12}$ alkylbenzene. Under these conditions, only monosulfonation of the phenyl moiety of the alkylbenzene occurs.

Suitable sulfonating agents which can be used include, for example, sulfur trioxide, sulfuric acid, chlorosulfonic acid, and the like. Suitable inert organic solvents which can be used include, for example, methylene chloride, dichloroethane, trichloroethane, tetrachloroethane, and the like. Also, although an organic solvent could be used, it is generally preferable to conduct the sulfonation neat.

Since the product of the sulfonation is an acid, i.e.,

(I)

wherein R is $C_{12}$ alkyl it is necessary to neutralize the acid to permit its use as a detergent. The sulfonic acid product (I) can be neutralized by simple neutralization with a base to yield the corresponding sulfonate salt. The neutralization can be conveniently conducted in situ with the sulfonation reaction product mixture. (Any excess sulfonating agent can be simply neutralized in situ along with the sulfonic acid product (I).)

Typically, the neutralization is conducted at temperatures in the range of about from 0° to 60° C. and pressures of about from 1 to 2 atmospheres using about from 1 to 1.1 mole equivalents of base per mole equivalent of sulfonate in the alkylbenzene. Suitable bases which can be used include, for example, alkali metal hydroxides, alkali earth hydroxides, ammonium hydroxides, quaternary ammonium hydroxides, amines, and the like. Typically, the base is added as an aqueous solution. Generally, the selection of the base will be a matter of economics, and for this reason, sodium hydroxide is preferred because it gives good results and is relatively inexpensive. Suitable inert organic solvents which can be used include the same solvents as listed above with respect to the sulfonation. However, typically a solvent is not used because generally it is not necessary and merely adds another separation step to remove the solvent.

The $C_{12}$ alkylbenzene sulfonate can be recovered from the reaction mixture by any suitable procedure or the reaction mixture can be simply concentrated by evaporating off water added with the base. Any small amounts of unreacted $C_{12}$ alkylbenzene in the reaction product can be removed by a variety of procedures used in the detergent art, etc., including extraction.

In the case where the $C_{12}$ olefin used in the alkylation step was prepared using an intermediate $C_{12}$ olefin containing only 70 to 75 weight % linear hexene, the $C_{12}$ alkylbenzene and $C_{12}$ alkylbenzene sulfonate products will be mixtures of different $C_{12}$ alkylbenzene or $C_{12}$ alkylbenzene sulfonate salts containing a high proportion (e.g., 10 to 40 weight %, typically 15 to 35 weight %) of multibranched $C_{12}$ alkylbenzenes or $C_{12}$ alkylbenzene sulfonate salts. Despite the high proportion of multibranched $C_{12}$ alkylbenzene sulfonate salts, the overall mixture has good detergent properties and biodegradability.

The $C_{12}$ alkylbenzene sulfonates can be used as detergents in pure form or can be formulated with a variety of builders (sequestering agents) and/or additives such as, for example, are conventionally used in the detergent art.

The present processes and process steps can be conducted as batch, semi-continuous or continuous operations or as a combination of such operations.

It should also be appreciated that where typical or preferred process conditions (e.g., temperatures, times, mole ratios, catalyst ratios, etc.) have been given, that other process conditions could also be used. Optimum reaction conditions (e.g., temperature, reaction time, reactant ratios, catalyst ratios, solvents, etc.) may vary with the particular reactants, catalysts, or solvents used, but can be determined by routine optimization procedures.

A further understanding of the invention can be had from the following non-limiting examples.

EXAMPLES

EXAMPLE 1

In this example, seventy-five (75) g of propylene and 0.075 g of hexafluoroacetoacetyl nickel cyclooctadiene were charged to an autoclave under anhydrous conditions under an Argon atmosphere. The mixture was heated at 75° C. for 2¾ hours affording 40 g of an oligomeric product consisting of 87 weight % $C_6$ olefins and 12 weight % $C_9$ olefins. The excess propylene was vented and the hexenes isolated by distillation. These hexenes consisted of a mixture of n-hexenes and methylpentenes as described in Table 1 hereinbelow. Eighty (80) g of this hexene mixture with a linear content of 75% was dimerized with 0.37 g of hexafluoroacetoacetyl nickel cyclooctadiene at 65° to 70° C. to obtain a 51% conversion of hexenes with a selectivity to dodecenes of 90%. The dodecenes product was isolated from the unreacted hexenes and heavier oligomers by distillation. The overall selectivity to dodecenes based on propylene feedstock is 78%. This dodecene will be referred to as Olefin I.

EXAMPLE 1-A

In this example, the same procedure as used in Example 1 was used except that the intermediate hexenes were extracted with sulfuric acid. The $C_6$ olefins that have a 75% linear content were contacted with a 1.7:1 weight ratio of 66 vol % aqueous sulfuric acid to hydrocarbon for 5 minutes at 20° C. with vigorous stirring. Once stirring ceased, phase separation was immediate and the hydrocarbon phase was separated from the acid phase. The recovered hexene phase was dried over 5A molecular sieves and degassed. Analysis of a sample of this product by hydrogenation indicated that the linear content of the hexenes had been enriched to 90%. Analysis by gas chromatography indicated that only incipient tertiary carbonium ion olefins such as 2-methyl-2-penetene and 2-methyl-1-pentene were removed by the acid treatment. The hexene distribution after the acid extraction is shown in Table 1. The enriched hexenes were then dimerized in the same manner as dimerized in Example 1. The overall selectivity to dodecenes from propylene feedstock was 65% in this example.

EXAMPLE 2

This example illustrates the improvement in the catalyst life of the second dimerization step catalyst afforded by extracting the $C_6$ feed with sulfuric acid prior to dimerization.

In this example, 5.6 g of the acid treated, intermediate $C_6$-olefin product of Example 1-A was dimerized at 69° C. using a hexafluoroacetylacetone catalyst using substantially the same reaction conditions as were used for the second step polymerization in Example 1. For comparison purposes, 5.6 g of a $C_6$-intermediate product containing 75% by weight n-hexenes and 25% by weight methylpentenes was dimerized in the same manner as the acid-treated intermediate product.

After 7 hours, 342 turnovers were obtained for the dimerization using the acid extracted $C_6$ olefin monomer versus only 142 turnovers where the olefin monomer was not extracted. At the end of 7 hours, the product from the acid extracted product contained 89 weight % semi-linear $C_{12}$ olefins versus only 80 weight % where the $C_6$ olefin monomer was not acid extracted.

EXAMPLE 3

In this example, the same procedure as in Example 1-A was generally followed except that an alkyl aluminum halide-promoted nickel carboxylate catalyst was used to dimerize the enriched hexenes intermediate. Twenty-four (24) g of hexenes was dimerized with 0.036 g of 2-ethylhexanoate nickel o-chlorobenzoate promoted by 0.127 g of ethyl aluminum dichloride and 0.026 g of triphenyl phosphine. The dimerization was carried out at 25° to 35° C. for 2 hours resulting in 55% conversion of hexenes with a selectivity to dodecenes of 93%. The dodecenes were isolated from the unconverted hexenes and heavier oligomers by distillation. The overall selectivity to dodecenes from propylene feedstock was 67%.

EXAMPLE 4

In this example, the same procedure as used in Example 3 was used except that a nickel carbonyl-promoted

TABLE 1
Composition of $C_6$ Olefin Isomers Feed for Second Stage Dimerization

| $C_6$ Olefin | Boiling Points | Example 1* | Example 2* | U.S.Pat. No. 3,317,628 Run III* |
|---|---|---|---|---|
| 4-methylpent-1-ene | 53.7 | 1.2 | 0.8 | 4.8 |
| cis-4-methylpent-2-ene | 58.1 | 2.1 | 1.1 | 14.3 |
| trans-4-methylpent-2-ene | 54.7 | 3.1 | 4.1 | 20.9 |
| 2,3-dimethylbut-1-ene | 56.3 | 0.6 | 0.8 | 0.4 |
| 2-methylpent-1-ene | 61.7 | 4.8 | 0.1 | 4.4 |
| 1-hexene | 63.5 | 3.7 | 2.5 | 2.7 |
| cis-3-hexane | 67.5 | 5.5 | 9.7 | 1.1 |
| trans-3-hexene | 70.5 | 8.7 | 20.4 | 3.0 |
| trans-2-hexene | 67.9 | 31.0 | 45.0 | 29.7 |
| 2-methylpent-2-ene | 67.4 | 13.5 | 1.4 | 1.0 |
| cis-2-hexene | 68.1 | 25.8 | 14.2 | 17.6 |

*Weight Percent aluminum chloride catalyst was used to dimerize the enriched hexenes intermediate. Fifteen (15) g of hexenes was dimerized with 0.04 g of aluminum trichloride and 0.076 g bis-triphenyl phosphine nickel dicarbonyl in 3.0 g of dichloromethane. The reaction was carried out at 25° to 35° C. for 3 hours to give 47% conversion of hexenes with a selectivity to dodecenes of 97%. The dodecenes were isolated from the unconverted hexenes and heavier oligomers as before. The overall selectivity to dodecenes from the propylene feedstock is 70% in this example.

EXAMPLE 5

This example demonstrates the utility of the above olefins as intermediates for biodegradable alkyl benzene sulfonates and the production of such sulfonates.

In this example, 94 g of the dodecene product of Example 1 was mixed with 470 g of benzene. This mixture was gradually added to a reaction solution containing 470 g benzene and 300 g of anhydrous hydrogen fluoride in a well-stirred polyethylene reaction vessel such that the reaction temperature does not exceed 20° C. Reaction was complete after 1 hour. Phase separation occurred after stirring was stopped. The hydrocarbon layer was recovered and neutralized with caustic and washed with water and dried over sodium sulfate. GC analysis indicates that less than 1% of the dodecene had fragmented. The yield of dodecyl benzene alkylate based on dodecene was in excess of 99%. The excess benzene was stripped off and the dodecyl benzene was purified by distillation.

The dodecyl benzene product was sulfonated using standard $SO_3$/air sulfonation reaction conditions. The alkylbenzene is sulfonated in a well-stirred water jacketed reactor equipped with a gas immersion inlet tube. A 10% molar excess of $SO_3$ is added at a rate of about ½ g/minute (for a 100-g batch of alkylate) as a 6% mixture in dry air through the gas immersion inlet tube. Run temperature is maintained between 35° and 50° C. by the 35° C. water jacket. After the $SO_3$ has been added, the sulfonate mixture is cooled, diluted with water and neutralized with sodium hydroxide until the pH is 7.5–8.0. This alkylbenzene sulfonate will be referred to as ABS-I.

By following the same general procedure, the dodecene product of Example 1-A was reacted with benzene and then sulfonated. The yields were again nearly quantitative based on the dodecene reacted. The sulfonate product will be referred to as ABS-II.

The biodegradability of ABS-I and ABS-II was determined using a hybrid modification of the standard ASTM test method designated biodegradability of alkyl-benzene sulfonates, ASTM D 2667 and the Standard OECD Screening Test for primary biodegradability of synthetic surface-active agents. This test measures biodegradability by measuring loss of specific surface activity of the alkylbenzene sulfonate. Thus, the greater the loss of surfactant activity, the greater the biodegradability. The results of this test are shown in Table A hereinbelow in terms of percent retention of surface activity as compared with the original material. Hence, the lower the percent retention the greater the biodegradability. In addition to samples ABS-I and ABS-II, a comparison standard linear alkylbenzene sulfonate known to be biodegradable and a standard branched alkylbenzene sulfonate known to be relatively nonbiodegradable were also tested.

The samples were tested at a concentration of between 2 to 20 ppm in a standard nutrient solution. The solutions were inoculated with a 1% solution of sewage effluent to initiate biodegradability. Surface activity was measured using the ASTM D 2330-82 procedure for methylene blue active substances. The results of the biodegradation tests are shown in Table A as a function of time after inoculation.

TABLE A

|  | Percent Surface Activity Remaining | |
|---|---|---|
|  | Day 7 | Day 10 |
| Linear Alkylbenzene Sulfonate | 5 | 3 |
| Branched Alkylbenzene Sulfonate | 88 | 65 |
| ABS-I, 73% | 8 | 6 |
| ABS-III, 88% | 9 | 6 |

As can be seen from the results recorded in Table A, both ABS-I and ABS-II exhibited good biodegradability.

Obviously, many modifications and variations of the invention described hereinabove and below can be made without departing from the essence and scope thereof.

What is claimed is:

1. A process for preparing $C_{12}$ semi-linear olefins consisting essentially of the steps of:
   (a) contacting a propylene feed with a selective dimerization catalyst, selective to the production of higher olefins, under dimerization conditions to produce a higher olefin product containing at least 60% by weight linear hexenes, under dimerization conditions and wherein said selective dimerization catalyst is selected from the group of:
   (1) a complex of a nickel chelate having the formula

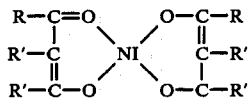

wherein R and R' independently are hydrogen, alkyl or aryl of up to 10 carbon atoms, or haloalkyl or haloaryl of up to 10 carbon atoms, with the proviso that the two R' groups of each chelating ligand together with the adjacent carbon atoms to which they are attached, can form a six-membered carbocyclic aromatic ring or a halogen substituted six-membered carbocyclic aromatic ring have 1 to 4 halogen substituents selected from the group of fluoro, chloro, bromo or iodo; with an alkyl aluminum alkoxide having the formula

wherein each R" independently is alkyl of up to 10 carbon atoms, preferably of up to 4 carbon atoms, m is a whole number from 1 to 2 inclusive and n is a whole number from 1 to 2 inclusive selected so that the sum of m and n equals 3;
   (2) a complex of bis(1,5-cyclooctadiene)nickel(O) with hexafluoro-2,4-pentanedione; and
   (3) a complex comprising transition metal complex selected from complexes of nickel and palladium with a fluoro-organic thiol or sulfide ligand, having a single sulfur atom in a ligating position and wherein the carbon atom adjacent the carbon atom to which the sulfur atom is attached has at least one fluoro substituent and with the proviso that said fluoro-organic thiol or sulfide does not contain any other ligating group or atom in a ligating position which will displace fluoro as a ligand, and an organometallic-reducing agent selected from the group of borohydride and organoaluminum halides and alkoxides having the formula $R^*_m AlX_n$ wherein $R^*$ is alkyl, aryl or arylalkyl; X is fluoro chloride, bromide, iodide or alkoxide and m is 1 or 2 and n is 3-m;
   (b) fractionally distilling the reaction product of step (a) to recover a $C_6$ olefin fraction containing linear hexenes and branched $C_6$ olefins and wherein said fraction contains 70 to 82% by weight of linear hexenes; and
   (c) contacting the $C_6$ olefin fraction of step (b) with a dimerization catalyst under dimerization conditions thereby producing a semi-linear $C_{12}$ olefins product containing at least 60% by weight linear dodecenes and mono-branched $C_{12}$ olefins.

2. The process of claim 1 wherein the dimerization catalyst of step (a) is selected from the group of hexafluoroacetoacetyl nickel cyclooctadiene; bis[pentafluorophenylthio]nickel with triethyl aluminum sesquichloride; and hexafluoroacetoacetyl nickel 2-ethylhexacetate with diethyl aluminum ethoxide.

3. The process of claim 2 wherein said dimerization of step (a) is conducted at temperatures in the range of about from 30° to 100° C. and pressures in the range of about from 1 to 50 atmospheres.

4. The process of claim 1 wherein said dimerization catalyst of step (c) is independently selected from the same group of catalysts as the dimerization catalyst of step (a).

5. The process of claim 4 wherein said dimerization of step (c) is conducted at temperatures in the range of 0° to 100° C. and pressures in the range of 1 to 10 atmospheres.

6. The process of claim 5 wherein the dimerization catalyst of step (a) is selected from the group of hexafluoroacetoacetyl nickel cyclooctadiene; bis[pentafluorophenylthio]nickel with triethyl aluminum sesquichloride; and hexafluoroacetoacetyl nickel 2-ethylhexacetate with diethyl aluminum ethoxide.

7. The process of claim 6 wherein said dimerization of step (a) is conducted at temperatures in the range of about 30° to 100° C. and pressures in the range of 1 to 50 atmospheres.

8. The process of claim 1 wherein the $C_6$ olefin fraction of step (b) contains about from 75 to 82% by weight of linear hexenes.

9. The process of claim 1 wherein the $C_6$ olefin fraction of step (b) contains about from 70 to 75% by weight of linear hexene.

10. The process of claim 1 wherein the dimerization catalyst of step (a) is selected from the group defined in group (3) and wherein said fluoro-organic thiol or sulfide is selected from the group having the formula $R_1SR$ wherein $R_1$ is fluoroalkyl having 1 to 18 fluoro atoms and 1 to 8 carbon atoms; fluoroaryl having 6 to 10 carbon atoms and 1 to 6 fluoro atoms; fluoroalkenyl having 2 to 8 carbon atoms and 1 to 16 fluoro atoms; fluoroalkanoyl having 2 to 8 carbon atoms and 1 to 15 fluoro atoms, fluoroalkanoylalkylene having 1 to 17 fluoro atoms and having 2 to 8 carbon atoms in the alkanoyl moiety and 1 to 6 carbon atoms in the alkylene moiety or fluorobenzoyl having 1 to 5 fluoro atoms or a substituted group selected from the fluoro-substituted groups set forth above, further substituted with 1 to 6 substituents independently selected from the group of lower alkyl, lower haloalkyl having 1 to 4 halo substituents, halo, lower haloalkenyl having 1 to 4 halo substituents, or lower alkoxy; and R is hydrogen, $C_1$–$C_8$ alkyl; $C_2$–$C_8$ alkenyl, aryl having 6 to 10 carbon atoms or arylalkyl, having 6 to 10 carbon atoms in aryl moiety and 1 to 4 carbon atoms in the alkyl moiety; alkanoyl having 2 to 8 carbon atoms; alkanoylalkylene having 2 to 8 carbon atoms in the alkanoyl moiety and 1 to 4 carbon atoms in the alkylene moiety; or a substituted group selected from the same groups as set forth hereinabove with respect to R substituted with from 1 to 6 substituents independently selected from the group of lower alkyl, lower haloalkyl having 1 to 4 halo substituents, halo, lower haloalkenyl having 1 to 4 halo substituents or lower alkoxy.

11. A process for preparing $C_{12}$ semi-linear olefins which comprises the steps of:
   (a) contacting a propylene feed containing at least about 90% by weight propylene with a selective dimerization catalyst selected from the group of hexafluoroacetoacetyl nickel cyclooctyldiene or bis[pentafluorophenylthio]nickel with triethyl aluminum sesquichloride under dimerization conditions at temperatures in the range of about from 50° to 80° C. and pressures in the range of about 10 to 40 atmospheres using a catalyst ratio in the range of about from 1,000 to 50,000 mole of propylene per mole of catalyst to yield dimer product containing at least about 60% by weight of linear hexenes and the remainder higher olefins, branched $C_6$ olefins and unreacted propylene;
   (b) fractionally distilling the reaction product of step (a) to recover a $C_6$ olefin fraction containing about from 70 to 82% by weight linear hexenes;
   (c) contacting the $C_6$ olefin fraction product of step (b) with a dimerization catalyst selected from the group of hexafluoroacetoacetyl nickel cyclooctadiene; bis[pentafluorophenylthio]nickel with triethyl aluminum sesquichloride; bis[triphenylphosphino]nickel dicarbonyl with aluminum chloride; nickel 2-ethylhexanoate trifluoroacetate with diethyl bis-aluminum tetrachloride; and nickel 2-ethylhexanoate trifluoroacetate with ethyl aluminum at temperatures in the range of about from 10° to 80° C. and pressures in the range of about from 1 to 5 atmospheres and a catalyst ratio in the range of about from 500 to 5,000 moles of $C_6$ olefin fraction per mole of catalyst to produce a semi-linear $C_{12}$ olefin product containing at least 60% by weight of linear dodecenes and mono-branched $C_{12}$ olefins.

12. The process of claim 11 wherein said $C_6$ olefin fraction contacted in step (c) contains about 70 to 75 weight % linear hexenes.

13. A process for preparing $C_{12}$ semi-linear olefins comprising the steps of:
   (a) contacting a propylene feed with a selective dimerization catalyst, selective to the production of higher olefins, under dimerization conditions to produce a higher olefin product containing at least 60% by weight linear hexenes, under dimerization conditions and wherein said selective dimerization catalyst is selected from the group of:
      (1) a complex of a nickel chelate having the formula

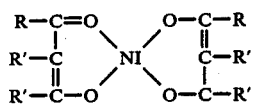

wherein R and R' independently are hydrogen, alkyl or aryl of up to 10 carbon atoms, or haloalkyl or haloaryl of up to 10 carbon atoms, with the proviso that the two R' groups of each chelating ligand together with the adjacent carbon atoms to which they are attached, can form a six-membered carbocyclic aromatic ring or a halogen substituted six-membered carbocyclic aromatic ring have 1 to 4 halogen substituents selected from the group of fluoro, chloro, bromo or iodo; with an alkyl aluminum alkoxide having the formula $(R'')_m Al(OR'')_n$ wherein each R'' independently is alkyl of up to 10 carbon atoms, preferably of up to 4 carbon atoms, m is a whole number from 1 to 2 inclusive and n is a whole number from 1 to 2 inclusive selected so that the sum of m and n equals 3;
      (2) a complex of bis(1,5-cyclooctadiene)nickel(O) with hexafluoro-2,4-pentanedione; and
      (3) a complex comprising transition metal complex selected from complexes of nickel and palladium with a fluoro-organic thiol or sulfide ligand, having a single sulfur atom in a ligating position and wherein the carbon atom adjacent the carbon atom to which the sulfur atom is attached has at least one fluoro substituent and with the proviso that said fluoro-organic thiol or sulfide does not contain any other ligating group or atom in a ligating position which will displace fluoro as a ligand, and an organometallic-reducing agent selected from the group of borohydride and organoaluminum halides and alkoxides having the formula $R^*_m AlX_n$ wherein $R^*$ is alkyl, aryl or arylalkyl; X is fluoro chloride, bromide, iodide or alkoxide and m is 1 or 2 and n is 3–m;
   (b) fractionally distilling the reaction product of step (a) to recover a $C_6$ olefin fraction containing linear hexenes and branched $C_6$ olefins and wherein said fraction contains 70 to 82% by weight of linear hexenes;
   (c) treating the $C_6$ olefin fraction recovered from step (b) with aqueous sulfuric acid at under reactive conditions at temperatures below about 30° C. thereby yielding a two liquid phase mixture comprising a $C_6$ olefin phase having a linear olefin content of at least about 80% by weight and an aqueous phase containing soluble nonlinear olefin sulfonates and recovering said $C_6$ olefin phase from said aqueous phase; and
   (d) contacting the $C_6$ olefin phase recovered in step (c) with a dimerization catalyst under dimerization conditions thereby producing a semi-linear $C_{12}$ olefin product containing at least 75% by weight linear dodecenes and mono-branched $C_{12}$ olefins.

14. A process for preparing $C_{12}$ semi-linear olefins which comprises the steps of:

(a) contacting a propylene feed containing at least about 90% by weight propylene with a selective dimerization catalyst selected from the group of hexafluoroacetoacetyl nickel cyclooctyldiene or bis[pentafluorophenylthio]nickel with triethyl aluminum sesquichloride under dimerization conditions at temperatures in the range of about from 50° to 80° C. and pressures in the range of about 10 to 40 atmospheres using a catalyst ratio in the range of about from 1,000 to 50,000 mole of propylene per mole of catalyst to yield dimer product containing at least about 60% by weight of linear hexenes and the remainder higher olefins, branched $C_6$ olefins and unreacted propylene;

(b) fractionally distilling the reaction product of step (a) to recover a $C_6$ olefin fraction containing about from 70 to 82% by weight linear hexenes;

(c) treating the $C_6$ olefin fraction recovered from step (b) with aqueous sulfuric acid under reactive conditions at temperature below about 30° C. to yield a two liquid phase mixture comprising a $C_6$ olefin phase having a linear olefin content of at least about 80% by weight and an aqueous phase containing soluble non-linear olefin sulfonates and recovering said $C_6$ olefin phase from said aqueous phase; and (d) contacting the $C_6$ olefin phase recovered in step (c) with a dimerization catalyst selected from the group of hexafluoroacetoacetyl nickel cyclooctadiene; bis[pentafluorophenylthio]nickel with triethyl aluminum sesquichloride; bis[triphenylphosphino]nickel dicarbonyl with aluminum chloride; nickel 2-ethylhexanoate trifluoroacetate with diethyl bis-aluminum tetrachloride; and nickel 2-ethylhexanoate trifluoroacetate with ethyl aluminum complexes at temperatures in the range of about from 10° to 80° C. and pressures in the range of about from 1 to 5 atmospheres and a catalyst ratio in the range of about from 500 to 5,000 moles of $C_6$ olefin per mole of catalyst to produce a semi-linear $C_{12}$ olefin product containing at least 75% by weight of linear dodecenes and mono-branched $C_{12}$ olefins.

15. A process for preparing $C_{12}$ semi-linear alkylbenzene sulfonates consisting essentially of the steps of:

(a) contacting a propylene feed with a selective dimerization catalyst, selective to the production of higher olefins, under dimerization conditions to produce a higher olefin product containing at least 60% by weight linear hexenes, under dimerization conditions and wherein said selective dimerization catalysts is selected from the group of:

(1) a complex of a nickel chelate having the formula

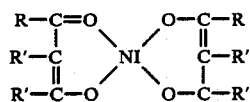

wherein R and R' independently are hydrogen, alkyl or aryl of up to 10 carbon atoms, or haloalkyl or haloaryl of up to 10 carbon atoms, with the proviso that the two R' groups of each chelating ligand together with the adjacent carbon atoms to which they are attached, can form a six-membered carbocyclic aromatic ring or a halogen substituted six-membered carbocyclic aromatic ring have 1 to 4 halogen substituents selected from the group of fluoro, chloro, bromo or iodo; with an alkyl aluminum alkoxide having the formula $(R'')_m Al(OR'')_n$ wherein each R'' independently is alkyl of up to 10 carbon atoms, preferably of up to 4 carbon atoms, m is a whole number from 1 to 2 inclusive and n is a whole number from 1 to 2 inclusive selected so that the sum of m and n equals 3;

(2) a complex of bis(1,5-cyclooctadiene)nickel(O) with hexafluoro-2,4-pentanedione; and (3) a complex comprising transition metal complex selected from complexes of nickel and palladium with a fluoro-organic thiol or sulfide ligand, having a single sulfur atom in a ligating position and wherein the carbon atom adjacent the carbon atom to which the sulfur atom is attached has at least one fluoro substituent and with the proviso that said fluoro-organic thiol or sulfide does not contain any other ligating group or atom in a ligating position which will displace fluoro as a ligand, and an organometallic-reducing agent selected from the group of borohydride and organoaluminum halides and alkoxides having the formula $R^*_m AlX_n$ wherein $R^*$ is alkyl, aryl or arylalkyl; X is fluoro chloride, bromide, iodide or alkoxide and m is 1 or 2 and n is 3-m;

(b) fractionally distilling the reaction product of step (a) to recover a $C_6$ olefin fraction containing linear hexenes and branched $C_6$ olefins and wherein said fraction contains 70 to 82% by weight of linear hexenes;

(c) contacting the $C_6$ olefin fraction of step (b) with a dimerization catalyst under dimerization conditions thereby producing a semi-linear $C_{12}$ olefins product containing at least 60% by weight linear dodecenes and mono-branched $C_{12}$ olefins;

(d) recovering the semi-linear $C_{12}$ olefin of step (c) and contacting said semi-linear $C_{12}$ olefins with benzene in the presence of an alkylation catalyst under reactive conditions thereby producing a mixture of semi-linear $C_{12}$ alkylbenzenes; and (e) recovering said semi-linear $C_{12}$ alkylbenzenes and contacting said recovered semi-linear $C_{12}$ alkylbenzenes with about from 1 to 1.5 moles, based on sulfur content, of a sulfonating agent per mole of said semi-linear $C_{12}$ alkylbenzenes under reactive conditions thereby producing the corresponding mixture of semi-linear $C_{12}$ alkylbenzene sulfonic acids having the general formula

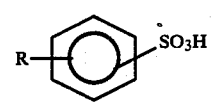

(I)

wherein R is semi-linear $C_{12}$ alkyl wherein R is semi-linear $C_{12}$ alkyl and neutralizing said semi-linear $C_{12}$ alkylbenzene sulfonic acids to yield the corresponding mixture of semi-linear $C_{12}$ alkylbenzene sulfonate salts.

16. The process of claim 15 wherein said semi-linear $C_{12}$ alkylbenzene sulfonic acids are neutralized in said step (e) with sodium hydroxide to yield the corresponding sodium semi-linear $C_{12}$ alkylbenzene sulfonates.

17. A process for preparing a mixture of semi-linear $C_{12}$ alkylbenzenes containing at least 60% by weight of linear and mono-branched $C_{12}$ alkylbenzenes and 10 to 40 weight % of multibranched $C_{12}$ alkylbenzenes, consisting essentially of the steps of:
   (a) contacting a propylene feed with a selective dimerization catalyst, selective to the production of higher olefins, under dimerization conditions to produce a higher olefin product containing at least 60% by weight linear hexenes, under dimerization conditions and wherein said selective dimerization catalyst is selected from the group of:
      (1) a complex of a nickel chelate having the formula

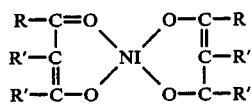

wherein R and R' independently are hydrogen, alkyl or aryl of up to 10 carbon atoms, or haloalkyl or haloaryl of up to 10 carbon atoms, with the proviso that the two R' groups of each chelating ligand together with the adjacent carbon atoms to which they are attached, can form a six-membered carbocyclic aromatic ring or a halogen substituted six-membered carbocyclic aromatic ring have 1 to 4 halogen substituents selected from the group of fluoro, chloro, bromo or iodo; with an alkyl aluminum alkoxide having the formula $(R'')_m Al(OR'')_n$ wherein each R'' independently is alkyl of up to 10 carbon atoms, preferably of up to 4 carbon atoms, m is a whole number from 1 to 2 inclusive and n is a whole number from 1 to 2 inclusive selected so that the sum of m and n equals 3;
      (2) a complex of bis(1,5-cyclooctadiene)nickel(O) with hexafluoro-2,4-pentanedione; and
      (3) a complex comprising transition metal complex selected from complexes of nickel and palladium with a fluoro-organic thiol or sulfide ligand, having a single sulfur atom in a ligating position and wherein the carbon atom adjacent the carbon atom to which the sulfur atom is attached has at least one fluoro substituent and with the proviso that said fluoro-organic thiol or sulfide does not contain any other ligating group or atom in a ligating position which will displace fluoro as a ligand, and an organometallic reducing agent selected from the group of borohydride and organoaluminum halides and alkoxides having the formula $R^*_m AlX_n$ wherein $R^*$ is alkyl, aryl or arylalkyl; X is fluoro chloride, bromide, iodide or alkoxide and m is 1 or 2 and n is 3-m;
   (b) fractionally distilling the reaction product of step (a) to recover a $C_6$ olefin fraction containing linear hexenes and branched $C_6$ olefins and wherein said fraction contains 70 to 75% by weight of linear hexenes; and
   (c) contacting the $C_6$ olefin fraction of step (b) with a dimerization catalyst under dimerization conditions thereby producing a semi-linear $C_{12}$ olefins product containing at least 60% by weight linear dodecenes and mono-branched $C_{12}$ olefins and 10 to 40% by weight multibranched $C_{12}$ olefins; and
   (d) recovering the semi-linear $C_{12}$ olefins product of step (c) and contacting the recovered semi-linear $C_{12}$ olefins product with benzene in the presence of an alkylation catalyst under reactive conditions thereby producing a mixture of semi-linear $C_{12}$ alkylbenzenes containing at least 60% by weight of linear and monobranched $C_{12}$ alkylbenzenes and 10 to 40 weight % of multibranched $C_{12}$ alkylbenzenes.

18. A process for preparing a mixture of semi-linear $C_{12}$ alkylbenzenes containing at least 60% by weight of linear and mono-branched $C_{12}$ alkylbenzenes consisting essentially of the steps of:
   (a) contacting a propylene feed containing at least about 90% by weight propylene with a selective dimerization catalyst selected from the group of hexafluoroacetoacetyl nickel cyclooctyldiene or bis[pentafluorophenylthio]nickel with triethyl aluminum sesquichloride under dimerization conditions at temperatures in the range of about from 50° to 80° C. and pressures in the range of about 10 to 40 atmospheres using a catalyst ratio in the range of about from 1,000 to 50,000 mole of propylene per mole of catalyst to yield dimer product containing at least about 60% by weight of linear hexenes and the remainder higher olefins, branched $C_6$ olefins and unreacted propylene;
   (b) fractionally distilling the reaction product of step (a) to recover a $C_6$ olefin fraction containing from 70 to 75% by weight linear hexenes;
   (c) contacting the $C_6$ olefin fraction product of step (b) with a dimerization catalyst selected from the group of hexafluoroacetoacetyl nickel cyclooctadiene; bis[pentafluorophenylthio]nickel with triethyl aluminum sesquichloride; bis[triphenylphosphino]nickel dicarbonyl with aluminum chloride; nickel 2-ethylhexanoate trifluoroacetate with diethyl bis-aluminum tetrachloride; and nickel 2-ethylhexanoate trifluoroacetate with ethyl aluminum at temperatures in the range of about from 10° to 80° C. and pressures in the range of about from 1 to 5 atmospheres and a catalyst ratio in the range of about from 500 to 5,000 moles of $C_6$ olefin fraction per mole of catalyst to produce a semi-linear $C_{12}$ olefin product containing at least 60% by weight of linear dodecenes and mono-branched $C_{12}$ olefins and 10 to 40 weight % multibranched $C_{12}$ olefins; and
   (d) recovering the semi-linear $C_{12}$ olefins of step (c) and contacting said semi-linear $C_{12}$ olefins with benzene in the presence of an alkylation catalyst under reactive conditions thereby producing a mixture of semi-linear $C_{12}$ alkylbenzenes containing at least 60 weight % of linear and mono-branched $C_{12}$ alkylbenzenes and 10 to 40 weight % multibranched $C_{12}$ alkylbenzenes.

19. The process of claim 18 wherein said alkylation catalyst of step (d) is hydrogen fluoride.

20. The process of claim 18 wherein said alkylation catalyst of step (d) is aluminum chloride.

21. A process for preparing a mixture of semi-linear $C_{12}$ alkylbenzene sulfonates containing at least weight % of linear and mono-branched alkylbenzene sulfonate and 10 to 40 weight % multibranched $C_{12}$ alkylbenzene sulfonates consisting essentially of the steps of:

(a) contacting a propylene feed with a selective dimerization catalyst, selective to the production of higher olefins, under dimerization conditions to produce a higher olefin product containing at least 60% by weight linear hexenes, under dimerization conditions and wherein said selective dimerization catalyst is selected from the group of:

(1) a complex of a nickel chelate having the formula

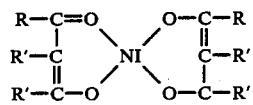

wherein R and R' independently are hydrogen, alkyl or aryl of up to 10 carbon atoms, or haloalkyl or haloaryl of up to 10 carbon atoms, with the proviso that the two R' groups of each chelating ligand together with the adjacent carbon atoms to which they are attached, can form a six-membered carbocyclic aromatic ring or a halogen substituted six-membered carbocyclic aromatic ring have 1 to 4 halogen substituents selected from the group of fluoro, chloro, bromo or iodo; with an alkyl aluminum alkoxide having the formula

$(R'')_m Al(OR'')_n$ wherein each R'' independently is alkyl of up to 10 carbon atoms, preferably of up to 4 carbon atoms, m is a whole number from 1 to 2 inclusive and n is a whole number from 1 to 2 inclusive selected so that the sum of m and n equals 3;

(2) a complex of bis(1,5-cyclooctadiene)nickel(O) with hexafluoro-2,4-pentanedione; and (3) a complex comprising transition metal complex selected from complexes of nickel and palladium with a fluoro-organic thiol or sulfide ligand, having a single sulfur atom in a ligating position and wherein the carbon atom adjacent the carbon atom to which the sulfur atom is attached has at least one fluoro substituent and with the proviso that said fluoro-organic thiol or sulfide does not contain any other ligating group or atom in a ligating position which will displace fluoro as a ligand, and an organometallic-reducing agent selected from the group of borohydride and organoaluminum halides and alkoxides having the formula $R^*_m AlX_n$ wherein $R^*$ is alkyl, aryl or arylalkyl; X is fluoro chloride, bromide, iodide or alkoxide and m is 1 or 2 and n is 3-m;

(b) fractionally distilling the reaction product of step (a) to recover a $C_6$ olefin fraction containing linear hexenes and branched $C_6$ olefins and wherein said fraction contains 70 to 75% by weight of linear hexenes; and (c) contacting the $C_6$ olefin fraction of step (b) with a dimerization catalyst under dimerization conditions thereby producing a semi-linear $C_{12}$ olefins product containing at least 60% by weight linear dodecenes and mono-branched $C_{12}$ olefins and 10 to 40% by weight multibranched olefins; and (d) recovering the semi-linear $C_{12}$ olefins of step (c) and contacting said semi-linear $C_{12}$ olefins with benzene in the presence of an alkylation catalyst under reactive conditions thereby producing a mixture of semi-linear $C_{12}$ alkylbenzenes containing at least 60% by weight of linear and mono-branched $C_{12}$ alkylbenzenes and 10 to 40 weight % of multibranched $C_{12}$ alkylbenzenes; and (e) recovering said semi-linear $C_{12}$ alkylbenzenes and contacting said recovered semi-linear $C_{12}$ alkylbenzenes with about from 1 to 1.5 moles, based on sulfur content, of a sulfonating agent per mole of said semi-linear $C_{12}$ alkylbenzenes under reactive conditions thereby producing the corresponding mixture of semi-linear $C_{12}$ alkylbenzene sulfonic acids having the general formula

wherein R is semi-linear $C_{12}$ alkyl wherein R is semi-linear $C_{12}$ alkyl and neutralizing said semi-linear $C_{12}$ alkylbenzene sulfonic acids to yield the corresponding mixture of semi-linear $C_{12}$ alkylbenzene sulfonate salts containing 10 to 40% by weight multibranched $C_{12}$ alkylbenzene sulfonate salts.

22. The process of claim 21 wherein said alkylation catalyst of step (d) is hydrogen fluoride.

23. The process of claim 22 wherein said neutralization of step (e) is conducted using a sodium base and said semi-linear $C_{12}$ alkylbenzene sulfonate is a sodium salt.

24. The process of claim 21 wherein said alkylation catalyst of step (d) is aluminum sulfate.

25. The process of claim 24 wherein said neutralization of step (e) is conducted using a sodium base and said semi-linear $C_{12}$ alkylbenzene sulfonate is a sodium salt.

26. A process for preparing semi-linear $C_{12}$ alkylbenzene sulfonates containing at least 75% by weight of linear and mono-branched $C_{12}$ alkylbenzene sulfonates which comprises the steps of:

(a) contacting a propylene feed with a selective dimerization catalyst, selective to the production of higher olefins, under dimerization conditions to produce a higher olefin product containing at least 60% by weight linear hexenes, under dimerization conditions and wherein said selective dimerization catalysts is selected from the group of:

(1) a complex of a nickel chelate having the formula

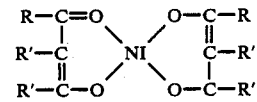

wherein R and R' independently are hydrogen, alkyl or aryl of up to 10 carbon atoms, or haloalkyl or haloaryl of up to 10 carbon atoms, with the proviso that the two R' groups of each chelating ligand together with the adjacent carbon atoms to which they are attached, can form a six-membered carbocyclic aromatic ring or a halogen substituted six-membered carbocyclic aromatic ring have 1 to 4 halogen substituents selected from the group of fluoro, chloro, bromo or iodo; with an alkyl aluminum alkoxide having the formula $$(R'')_m Al(OR'')_n$$

wherein each R" independently is alkyl of up to 10 carbon atoms, preferably of up to 4 carbon atoms, m is a whole number from 1 to 2 inclusive and n is a whole number from 1 to 2 inclusive selected so that the sum of m and n equals 3;

(2) a complex of bis(1,5-cyclooctadiene)nickel(O) with hexafluoro-2,4-pentanedione; and (3) a complex comprising transition metal complex selected from complexes of nickel and palladium with a fluoro-organic thiol or sulfide ligand, having a single sulfur atom in a ligating position and wherein the carbon atom adjacent the carbon atom to which the sulfur atom is attached has at least one fluoro substituent and with the proviso that said fluoro-organic thiol or sulfide does not contain any other ligating group or atom in a ligating position which will displace fluoro as a ligand, and an organometallic-reducing agent selected from the group of borohydride and organoaluminum halides and alkoxides having the formula $R^*_m AlX_n$ wherein $R^*$ is alkyl, aryl or arylalkyl; X is fluoro chloride, bromide, iodide or alkoxide and m is 1 or 2 and n is 3-m;

(b) fractionally distilling the reaction product of step (a) to recover a $C_6$ olefin fraction containing linear hexenes and branched $C_6$ olefins and wherein said fraction contains 70 to 82% by weight of linear hexenes;

(c) treating the $C_6$ olefin fraction recovered from step (b) with aqueous sulfuric acid under reactive conditions at temperatures below about 30° C. thereby yielding a two liquid phase mixture comprising a $C_6$ olefin phase having a linear olefin content of at least about 80% by weight and an aqueous phase containing soluble nonlinear olefin sulfonates and recovering said $C_6$ olefin phase from said aqueous phase;

(d) contacting the $C_6$ olefin phase recovered in step (c) with a dimerization catalyst under dimerization conditions thereby producing a semi-linear $C_{12}$ olefin product containing at least 75% by weight linear dodecenes and mono-branched $C_{12}$ olefins;

(e) recovering the semi-linear $C_{12}$ olefins of step (d) and contacting said semi-linear $C_{12}$ olefins with benzene in the presence of an alkylation catalyst under reactive conditions thereby producing a mixture of semi-linear $C_{12}$ alkylbenzenes corresponding to said $C_{12}$ olefins; and (f) recovering said semi-linear $C_{12}$ alkylbenzenes and contacting said recovered semi-linear $C_{12}$ alkylbenzenes with about from 1 to 1.5 moles, based on sulfur content, of a sulfonating agent per mole of said semi-linear $C_{12}$ alkylbenzenes under reactive conditions thereby producing the corresponding mixture of semi-linear $C_{12}$ alkylbenzene sulfonic acids having the general formula

(I)

wherein R is semi-linear $C_{12}$ alkyl and neutralizing said semi-linear $C_{12}$ alkylbenzene to yield the corresponding mixture of semi-linear $C_{12}$ alkylbenzene sulfonic acids sulfonate salts containing at least 75% by weight of linear and mono-branched $C_{12}$ alkylbenzene sulfonate salts.

27. The process of claim 26 wherein said alkylation catalyst of step (e) is hydrogen fluoride.

28. The process of claim 26 wherein said alkylation catalyst of step (e) is aluminum chloride.

29. A process for preparing semi-linear $C_{12}$ alkylbenzene sulfonates containing at least 75% by weight linear and mono-branched $C_{12}$ alkylbenzene sulfonates which comprises the steps of:

(a) contacting a propylene feed containing at least about 90% by weight propylene with a selective dimerization catalyst selected from the group of hexafluoroacetoacetyl nickel cyclooctyldiene or bis[pentafluorophenylthio]nickel with triethyl aluminum sesquichloride under dimerization conditions at temperatures in the range of about from 50° to 80° C. and pressures in the range of about 10 to 40 atmospheres using a catalyst ratio in the range of about from 1,000 to 50,000 mole of propylene per mole of catalyst to yield dimer product containing at least about 60% by weight of linear hexenes and the remainder higher olefins, branched $C_6$ olefins and unreacted propylene;

(b) fractionally distilling the reaction product of step (a) to recover a $C_6$ olefin fraction containing about from 70 to 82% by weight linear hexenes;

(c) treating the $C_6$ olefin fraction recovered from step (b) with aqueous sulfuric acid under reactive conditions at temperature below about 30° C. to yield a two liquid phase mixture comprising a $C_6$ olefin phase having a linear olefin content of at least about 80% by weight and an aqueous phase containing soluble non-linear olefin sulfonates and recovering said $C_6$ olefin phase from said aqueous phase;

(d) contacting the $C_6$ olefin phase recovered in step (c) with a dimerization catalyst selected from the group of hexafluoroacetoacetyl nickel cyclooctadiene; bis[pentafluorophenylthio]nickel with triethyl aluminum sesquichloride; bis[triphenylphosphino]nickel dicarbonyl with aluminum chloride; nickel 2-ethylhexanoate trifluoroacetate with diethyl bis-aluminum tetrachloride; and nickel 2-ethylhexanoate trifluoroacetate with ethyl aluminum complexes at temperatures in the range of about from 10° to 80° C. and pressures in the range of about from 1 to 5 atmospheres and a catalyst ratio in the range of about from 500 to 5,000 moles of $C_6$ olefin per mole of catalyst to produce a semi-linear $C_{12}$ olefin product containing at least 75% by weight of linear dodecenes and mono-branched $C_{12}$ olefins;

(e) recovering the semi-linear $C_{12}$ olefins of step (d) and contacting said semi-linear $C_{12}$ olefins with benzene in the presence of an alkylation catalyst under reactive conditions thereby producing a mixture of semi-linear $C_{12}$ alkylbenzenes corresponding to said $C_{12}$ olefins; and (f) recovering said semi-linear $C_{12}$ alkylbenzenes and contacting said recovered semi-linear $C_{12}$ alkylbenzenes with about from 1 to 1.5 moles, based on sulfur content, of a sulfonating agent per mole of said semi-linear $C_{12}$ alkylbenzenes under reactive conditions thereby producing the corresponding mixture of semi-linear $C_{12}$ alkylbenzene sulfonic acids having the general formula

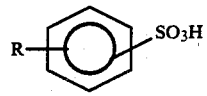
(I)

wherein R is semi-linear $C_{12}$ alkyl and neutralizing said semi-linear $C_{12}$ alkylbenzene to yield the corresponding mixture of semi-linear $C_{12}$ alkylbenzene sulfonate salts containing at least 75% by weight of linear and mono-branched $C_{12}$ alkylbenzene sulfonate salts.

30. The process of claim 29 wherein said alkylation catalyst of step (e) is hydrogen fluoride.

31. The process of claim 29 wherein said alkylation catalyst of step (e) is aluminum chloride.

* * * * *